US012735394B2

(12) United States Patent
Roh et al.

(10) Patent No.: US 12,735,394 B2
(45) Date of Patent: Sep. 15, 2026

(54) METHOD FOR PREPARING CYCLIC SULFONIC ACID ESTER DERIVATIVE COMPOUND

(71) Applicant: LG Chem, Ltd., Seoul (KR)

(72) Inventors: Sang Weon Roh, Daejeon (KR); Byung Soo Kang, Daejeon (KR); Min Su Hwang, Daejeon (KR); Jeong Ae Yoon, Daejeon (KR); Won Jae Lee, Daejeon (KR); Su Jeong Kim, Daejeon (KR)

(73) Assignee: LG Chem, Ltd., Seoul (KR)

( * ) Notice: Subject to any disclaimer, the term of this patent is extended or adjusted under 35 U.S.C. 154(b) by 470 days.

(21) Appl. No.: 18/574,536

(22) PCT Filed: Jan. 9, 2023

(86) PCT No.: PCT/KR2023/000350
§ 371 (c)(1),
(2) Date: Dec. 27, 2023

(87) PCT Pub. No.: WO2023/132713
PCT Pub. Date: Jul. 13, 2023

(65) Prior Publication Data

US 2024/0300915 A1 Sep. 12, 2024

(30) Foreign Application Priority Data

Jan. 10, 2022 (KR) ........................ 10-2022-0003553

(51) Int. Cl.
*C07D 327/04* (2006.01)
*C07C 327/36* (2006.01)

(52) U.S. Cl.
CPC .......... *C07D 327/04* (2013.01); *C07C 327/36* (2013.01)

(58) Field of Classification Search
CPC .... C07D 327/04; C07D 327/06; C07C 327/36
See application file for complete search history.

(56) References Cited

U.S. PATENT DOCUMENTS

| | | | |
|---|---|---|---|
| 2012/0130089 | A1 | 5/2012 | Kuramoto et al. |
| 2014/0142324 | A1 | 5/2014 | Kuramoto et al. |
| 2015/0110863 | A1 | 4/2015 | Khiar El Wahabi et al. |
| 2018/0155350 | A1 | 6/2018 | Hall et al. |
| 2019/0101825 | A1 | 4/2019 | Kawaue et al. |
| 2020/0239475 | A1 | 7/2020 | Hall et al. |

FOREIGN PATENT DOCUMENTS

| | | | |
|---|---|---|---|
| CN | 102471305 | A | 5/2012 |
| CN | 106632232 | A | 5/2017 |
| JP | 2006004813 | A | 1/2006 |
| JP | 2006156314 | A | 6/2006 |
| JP | 2014115627 | A | 6/2014 |
| JP | 2015514688 | A | 5/2015 |
| JP | 2020510617 | A | 4/2020 |
| KR | 20090076617 | A | 7/2009 |
| KR | 20120045027 | A | 5/2012 |
| KR | 20170066872 | A | 6/2017 |
| KR | 20190038351 | A | 4/2019 |
| KR | 20210110085 | A | 9/2021 |
| KR | 20210144572 | A | 11/2021 |

(Continued)

OTHER PUBLICATIONS

Ruairí O. McCourt and Eoin M. Scanlan Organic Letters 2019 21 (9), 3460-3464; DOI: 10.1021/acs.orglett.9b01271 (Year: 2019).*

McCourt, R. et al., "Atmospheric Oxygen Mediated Radical Hydrothiolation of Alkenes" Communication, Wiley-VCH, Chemistry—A European Journal, Jun. 2020, pp. 1-8.

King, J.F. et al., "Hydroxy-1-Alkanesulfonyl Chlorides" Phosphorous and Sulfur and the Related Elements, 1987, pp. 161-175, vol. 31, Issue 1-2.

(Continued)

*Primary Examiner* — Clinton A Brooks
*Assistant Examiner* — Josmalen M. Ramos-Lewis
(74) *Attorney, Agent, or Firm* — Lerner David LLP

(57) ABSTRACT

A manufacturing method capable of improving the yield and properties of a cyclic sulfonic acid ester derivative compound includes (A) reacting a compound represented by Formula 1 and thioacetic acid to prepare a compound represented by Formula 2, and (B) subjecting the compound represented by Formula 2 to an oxidative cyclization reaction to prepare a compound represented by Formula 3:

[Formula 1]

[Formula 2]

[Formula 3]

wherein m and $R_1$ to $R_8$ are described herein.

17 Claims, 2 Drawing Sheets

(56) References Cited

FOREIGN PATENT DOCUMENTS

KR 20220133684 A 10/2022

OTHER PUBLICATIONS

International Search Report for PCT/KR2023/000350 mailed Apr. 18, 2023. 3 pages.

Extended European Search Report including Written Opinion for Application No. 23737461.6 dated Oct. 22, 2024. 9 pgs.

* cited by examiner

METHOD FOR PREPARING CYCLIC SULFONIC ACID ESTER DERIVATIVE COMPOUND

CROSS-REFERENCE TO RELATED APPLICATIONS

This application is a national stage entry under 35 U.S.C. § 371 of International Application No. PCT/KR2023/000350 filed on Jan. 9, 2023, which claims priority from Korean Patent Application No. 10-2022-0003553 filed on Jan. 10, 2022, all the disclosures of which are incorporated by reference herein in its entirety.

TECHNICAL FIELD

The present disclosure relates to a method for preparing a cyclic sulfonic acid ester derivative compound.

BACKGROUND ART 1,3-propane sultone and 1,4-butane sultone are known as useful compounds as non-aqueous electrolyte additives in lithium secondary batteries. However, 1,3-propane sultone, and 1,4-butane sultone have problems such as toxicity issues, gas generation, and stability, and thus, studies on cyclic sulfonic acid ester derivative compounds that can be used as non-aqueous electrolyte additives are being actively conducted. For example, when a cyclic sulfonic acid ester derivative compound in which a substituent containing a hydroxy group is introduced at the gamma position of 1,3-propane sultone (the position of carbon next to oxygen in a ring structure) or a cyclic sulfonic acid ester derivative compound in which a substituent containing a hydroxy group is introduced at the delta position of 1,4-butane sultone (the position of carbon next to oxygen in a ring structure) is used as a non-aqueous electrolyte additive in a lithium secondary battery, an electrode-electrolyte interface that is stable at high temperatures and has low resistance may be formed to improve the lifespan properties of the lithium secondary battery.

Meanwhile, the cyclic sulfonic acid ester derivative compound is prepared by, for example, a) a hydrosulfonation reaction and b) a dehydration reaction of 3-butene-1,2-diol. However, it is difficult to purify a sulfonate, which is a hydrosulfonation reaction product of 3-butene-1,2-diol, from an inorganic salt by-product, and there is a problem in that a corrosive gas is generated by $SOCl_2$ used in the dehydration reaction. In addition, the overall yield is as low as less than 50% due to the purification issue in the process a) and the reactivity issue in the process b), and there is a problem in that a product is obtained in a black tar form (a black gum form).

Therefore, there is a need for research on a method for preparing a cyclic sulfonic acid ester derivative compound that can address the above-described problems.

Technical Problem

An aspect of the present invention is to improve the manufacturing process, yield, product properties, and the like of a cyclic sulfonic acid ester derivative compound.

Technical Solution

According to an aspect of the present invention, there is provided a method for preparing a cyclic sulfonic acid ester derivative compound.

(1) The present disclosure provides a method for preparing a cyclic sulfonic acid ester derivative compound, wherein the method includes (A) reacting a compound represented by Formula 1 below and a thioacetic acid to prepare a compound represented by Formula 2 below, and (B) subjecting the compound represented by Formula 2 above to an oxidative cyclization reaction to prepare a compound represented by Formula 3 below.

[Formula 1]

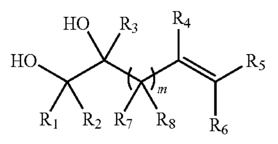

[Formula 2]

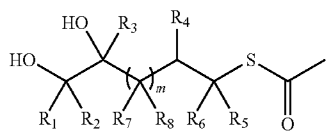

[Formula 3]

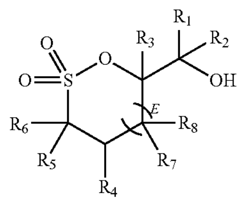

In Formula 1 to Formula 3, m is 0 or 1, and $R_1$ to $R_8$ are each independently hydrogen, or a substituted or unsubstituted $C_1$-$C_{10}$ alkyl group.

(2) In (1) above, the present disclosure provides a method for preparing a cyclic sulfonic acid ester derivative compound, wherein the equivalent ratio of the compound represented by Formula 1 above to the thioacetic acid is 1:1 to 1:3.

(3) In (1) or (2) above, the present disclosure provides a method for preparing a cyclic sulfonic acid ester derivative compound, wherein the step (A) is performed under an acid catalyst.

(4) In any one of (1) to (3) above, the present disclosure provides a method for preparing a cyclic sulfonic acid ester derivative compound, wherein the step (A) is performed in a polar aprotic solvent.

(5) In (4) above, the present disclosure provides a method for preparing a cyclic sulfonic acid ester derivative compound, wherein the polar aprotic solvent is one or more of dichloromethane, chloroform, 1,2-dichloroethane, or acetonitrile.

(6) In any one of (1) to (5) above, the present disclosure provides a method for preparing a cyclic sulfonic acid ester derivative compound, wherein the step (A) is performed at a temperature of 20° C. to 40° C.

(7) In any one of (1) to (6) above, the present disclosure provides a method for preparing a cyclic sulfonic acid ester derivative compound, wherein the step (B) is performed under an acid catalyst.

(8) In any one of (1) to (7) above, the present disclosure provides a method for preparing a cyclic sulfonic acid ester derivative compound, wherein the step (B) is performed in a polar protic solvent.

(9) In (8) above, the present disclosure provides a method for preparing a cyclic sulfonic acid ester derivative compound, wherein the polar protic solvent is one or more of distilled water, methanol, ethanol, propanol, or isopropanol.

(10) In any one of (1) to (9) above, the present disclosure provides a method for preparing a cyclic sulfonic acid ester derivative compound, wherein in the step (B), the oxidative cyclization reaction is performed under one or more oxidization agents selected from $H_2O_2$, HOCl, NCS, NBS, or $KHSO_5 \cdot 0.5KHSO_4 \cdot 0.5K_2SO_4$.

(11) In any one of (1) to (10) above, the present disclosure provides a method for preparing a cyclic sulfonic acid ester derivative compound, wherein the step (B) is performed at a temperature of 0° C. to 25° C.

Advantageous Effects

According to the present disclosure, it is possible to improve a preparation process of cyclic sulfonic acid ester derivative compounds, improve yields, and obtain products with improved properties.

DETAILED DESCRIPTION

Figure 1:
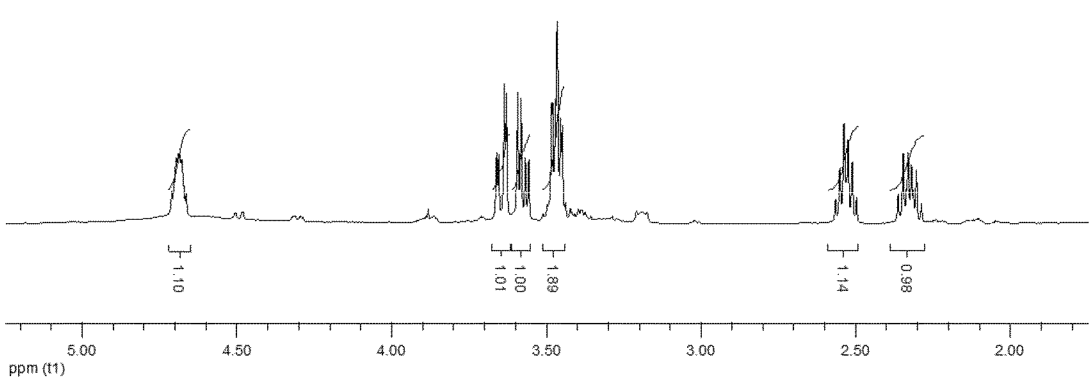
FIG. 1 is a $^1$H-NMR spectrum of a product prepared in Example 1.

Hereinafter, various embodiments of the present invention will be described in more detail to facilitate understanding of the present invention. In this case, it will be understood that words or terms used in the specification and claims shall not be interpreted as having the meaning defined in commonly used dictionaries. It will be further understood that the words or terms should be interpreted as having a meaning that is consistent with their meaning in the context of the relevant art and the technical idea of the invention, based on the principle that an inventor may properly define the meaning of the words or terms to best explain the invention.

One aspect of the present invention relates to a method for preparing a cyclic sulfonic acid ester derivative compound, wherein the method includes (A) reacting a compound represented by Formula 1 below with a thioacetic acid to prepare a compound represented by Formula 2 below, and (B) subjecting the compound represented by Formula 2 below to an oxidative cyclization reaction to prepare a compound represented by Formula 3.

[Formula 1]

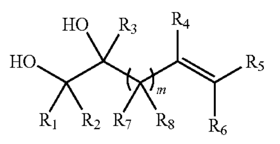

[Formula 2]

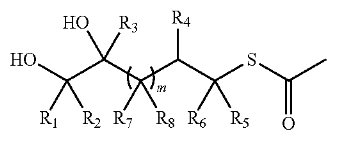

-continued

[Formula 3]

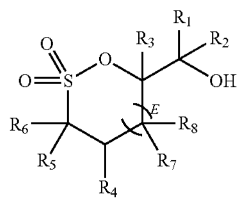

In Formula 1 to Formula 3, m is 0 or 1, and $R_1$ to $R_8$ are each independently hydrogen, or a substituted or unsubstituted $C_1$-$C_{10}$ alkyl group.

In the present disclosure, a substituent in the substituted alkyl group may be deuterium, a halogen group, a hydroxy group, a —COOR group (wherein R is an unsubstituted $C_1$-$C_6$ alkyl group), a $—SO_2NR'_2$ group (wherein R' is hydrogen or an unsubstituted $C_1$-$C_6$ alkyl group), a cyano group, or a straight or branched $C_1$-$C_6$ alkoxyl group.

In terms of ease of synthesis of Formula 3 above, the $R_1$ to $R_8$ may each independently be hydrogen, or an unsubstituted $C_1$-$C_6$ alkyl group. Specifically, the $R_1$ to $R_8$ may all be hydrogen in terms of each of synthesis and structural stability.

The compound represented by Formula 3 above may be a compound represented by Formula a or b below.

[Formula a]

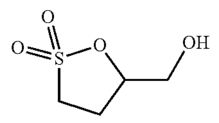

[Formula b]

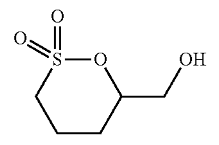

Hereinafter, each step of the method for preparing a cyclic sulfonic acid ester derivative compound will be described in detail.

Step (A)

The step (A) is a step in which a double bond of the compound represented by Formula 1 above and a thioacetic acid react (i.e., a thiol-ene reaction between a terminal alkene and thioacetic acid) to form a thioacetate intermediate.

According to the present disclosure, the equivalent ratio of the compound represented by Formula 1 above to the thioacetic acid above may be 1:1 to 1:3, specifically 1:1 to 1:2.5, more specifically 1:1 to 1:2. When the equivalent ratio of the compound represented by Formula 1 above and the thioacetic acid above is within the above range, a conversion rate of 99% or higher (a rate at which the compound represented by Formula 1 is converted to the compound represented by Formula 2) may be achieved without the generation of other identifiable by-products.

According to the present disclosure, the step (A) may be performed under an acid catalyst to promote proton transfer on the reaction mechanism. The acid catalyst may be, for example, trifluoroacetic acid (TFA), hydrochloric acid (HCl), sulfuric acid ($H_2SO_4$), or the like.

According to the present disclosure, the step (A) may be performed in a polar aprotic solvent to facilitate the generation of a radical intermediate in an appropriate amount.

According to the present disclosure, the polar aprotic solvent may be one or more of dichloromethane, chloroform, 1,2-dichloroethane, or acetonitrile. In this case, there is an advantage in that the radical intermediate is effectively generated without causing the solvent to participate in the reaction.

According to the present disclosure, the step (A) may be performed at a temperature of 20° C. to 40° C., specifically at a temperature of 30° C. to 40° C. In this case, the reaction speed of the step (A) may be fast, and a thioacetate intermediate (the compound represented by Formula 2) may not be decomposed.

The step (A) may be performed for 2 hours to 8 hours to maximize the reaction conversion rate while preventing the thioacetate intermediate from decomposing.

Step (B)

The step (B) is a step in which an oxidization agent is introduced to the compound represented by Formula 2, which is a reaction intermediate, to cause an oxidative cyclization reaction to occur, thereby forming a compound represented by Formula 3.

According to the present disclosure, the step (B) may be performed under an acid catalyst to maintain a pH that promotes an oxidation reaction. The acid catalyst in the step (B) may be added in an amount of 3 equivalents or more with respect to 1 equivalent of the compound represented by Formula 2 above. When the acid catalyst in the step (B) is, for example, HCl, the acid catalyst may act as an acid catalyst and also a $Cl^-$ source.

According to the present disclosure, the step (B) may be performed in a polar protic solvent to secure the solubility of the compound represented by Formula 2 above.

According to the present disclosure, the polar protic solvent may be one or more of distilled water, methanol, ethanol, propanol, or isopropanol. In this case, the reaction may proceed in a uniform phase of the compound (a reactant) represented by Formula 2 above, the oxidization agent, and the acid catalyst.

According to the present disclosure, in the step (B), the oxidative cyclization reaction may be performed under one or more oxidization agents selected from $H_2O_2$, HOCl, NCS, NBS, or $KHSO_5 \cdot 0.5KHSO_4 \cdot 0.5K_2SO_4$.

According to the present disclosure, the step (B) may be performed at a temperature of 0° C. to 25° C., specifically at a temperature of 0° C. to 15° C. In this case, an excessive oxidation reaction caused by the oxidization agent may be controlled to ensure reaction safety.

In order to prevent side reactions (e.g., a decomposition reaction of an oxidization agent itself, etc.) caused by the oxidization agent, the step (B) may be performed while controlling the temperature as follows. Specifically, in the step (B), the temperature is maintained at 0° C. to 10° C. when introducing the oxidization agent, and after the introduction of the oxidization agent is completed, the oxidative cyclization reaction may be performed at a temperature of 0° C. to 25° C.

The step (B) may be performed for 4 hours to 24 hours to maximize the yield within a range for preventing isomerization of the compound (a product) represented by Formula 3.

Meanwhile, in the step (B), the oxidization agent is added in excess, and after the reaction is completed, sodium sulfite ($Na_2SO_3$) may be introduced in order to quench the remaining oxidization agent. Through the quenching, the risk of explosion of the remaining oxidization agent may be prevented.

Hereinafter, embodiments of the present invention will be described in detail so that those skilled in the art may easily carry out the present invention. However, the present invention may be embodied in many different forms, and is not limited to the embodiments set forth herein.

EXAMPLES AND COMPARATIVE EXAMPLES

Example 1

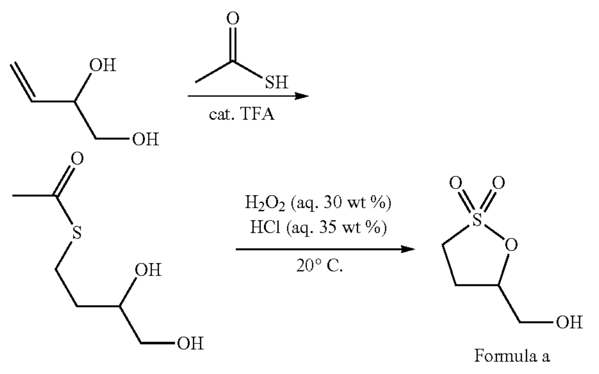

Formula a 52.8 g (1 equivalent) of 3-butene-1,2-diol, 91.3 g (2 equivalents) of thioacetic acid, 34.2 g (0.5 equivalents) of trifluoroacetic acid (TFA), and 100 ml of dichloromethane were introduced to a round-bottomed flask and reacted while being refluxed for 5 hours. Volatile organic substances were removed by vacuum to obtain 93.9 g (yield: 95.3%) of a thioacetate intermediate (S-(3,4-dihydroxybutyl)-1-yl thioacetate) in the form of a pale yellow liquid.

42 g of the thioacetate intermediate and 100 ml of MeOH were introduced to a new round-bottomed flask (hereinafter, a reactor), and then cooled to 0° C. While maintaining the temperature inside the reactor at 0° C., 68 ml of an aqueous solution of HCl having a concentration of 35 mass % was slowly added to the reactor, and then 84 ml of an aqueous solution of $H_2O_2$ having a concentration of 30 mass % was slowly added thereto. After the introduction of the $H_2O_2$ aqueous solution was completed, the mixture was stirred and reacted at 0° C. for 4 hours, and then after the temperature was elevated to 25° C., the mixture was stirred and reacted at 25° C. for 4 hours, followed by introducing 15 g of $Na_2SO_3$ thereto and the mixture was stirred for an additional 1 hour. A product was extracted with 200 ml of ethyl acetate (an organic layer was separated), and the product was further extracted from an aqueous layer (3 times with 100 ml of ethyl acetate). After collecting the organic layer, moisture was removed with $MgSO_4$ and distilled under reduced pressure to obtain 26.3 g (yield: 76.7) of the compound represented by Formula a in the form of a colorless solution.

Comparative Example 1

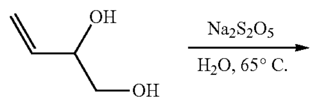

-continued

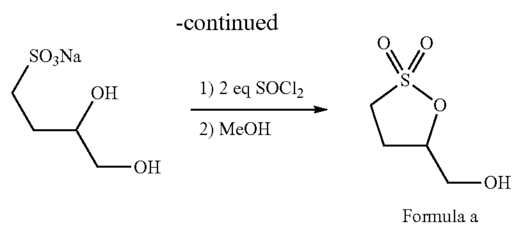

Formula a 20 g of 3-butene-1,2-diol and 90 ml of deionized (DI) water were added to a round-bottomed flask, and then while the mixture was vigorously stirred at 65° C., a $Na_2S_2O_5$ aqueous solution (a solution in which 59.4 g of $Na_2S_2O_5$ was dissolved in 100 ml of deionized water) neutralized with NaOH (20 g) was introduced thereto over 5 minutes. During the stirring, the pH was maintained between 7.3 and 7.6 using a 6M $H_2SO_4$ aqueous solution. When 3-butene-1,2-diol was exhausted, the solvent was removed by distillation under reduced pressure. 250 ml of MeOH was introduced to a white solid residue and the mixture was stirred for 2 hours. An insoluble inorganic substance was filtered out, and a solid inorganic salt was washed with 2500 ml of MeOH. A filtrate was distilled under reduced pressure to obtain 42 g (yield: 94%, purity: 55%) of a sulfonate intermediate (3,4-dihydroxybutane-1-sulfonic acid sodium salt) mixed with an inorganic salt.

1.9 g of the sulfonate intermediate was dispersed in 10 ml of a chloroform solution, and then 0.08 ml (0.1 equivalents) of DMF was introduced thereto. 1.5 ml (2 equivalents) of $SOCl_2$ was added dropwise at room temperature, and then stirred at 55° C. for 8 hours. After the reaction was completed, a reaction solution was cooled to room temperature, filtered to remove a solid by-product, and the filtrate was concentrated by distillation under reduced pressure. 10 ml of methanol and 0.8 ml of a 12M HCl were introduced to the concentrated solution at 0° C., and the mixture was stirred for 2 hours, hydrolyzed, and then distilled under reduced pressure to remove the solvent. An unpurified product was dissolved in dichloromethane (DCM), and 2 g of Celite was introduced thereto and stirred for 30 minutes, and after the celite was filter-treated, a filtrate was concentrated to obtain 0.55 g (yield: 36%) of the compound represented by Formula a in a black gum form.

EXPERIMENTAL EXAMPLES

Figure 2:
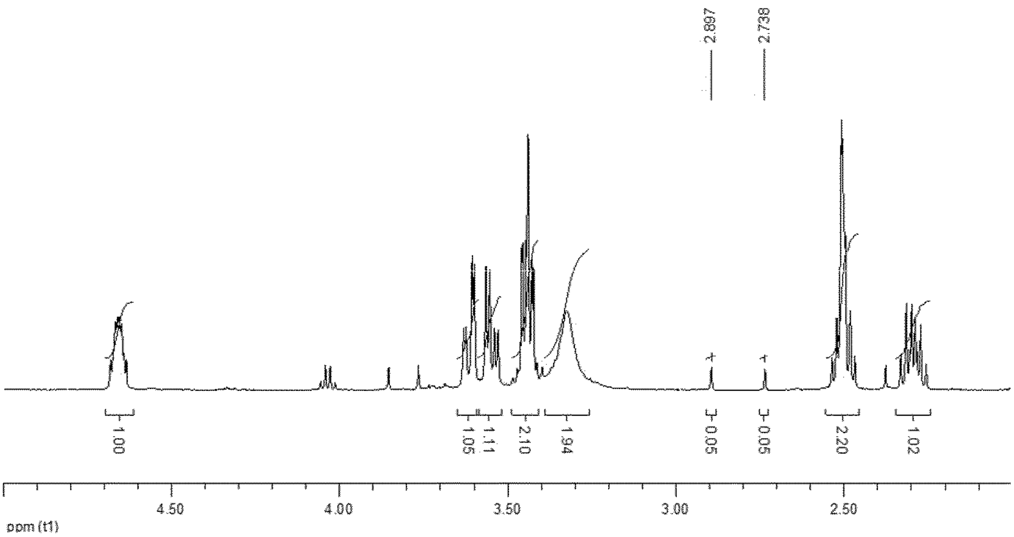
FIG. 2 is a $^1$H-NMR spectrum of a product prepared in Comparative Example 1.

After confirming that the thioacetate intermediate or the sulfonate intermediate was exhausted to TLC in Example 1 and Comparative Example 1, respectively, 0.05 ml of the solution in which the reaction was completed was taken and diluted with 0.45 ml of DMSO-d6, followed by obtaining a $^1$H-NMR spectrum using a nuclear magnetic resonance spectrometer (B500 Bruker Avace Neo, Bruker Co.), which is shown in FIG. 1 and FIG. 2, respectively.

Through the $^1$H-NMR spectrum, it was confirmed that the compound represented by Formula a was prepared in both Example 1 and Comparative Example 1, and in the case of Example 1, it was confirmed that the yield of the compound represented by Formula was 76.7%, which was higher than the yield (36%) in the case of Comparative Example 1.

From the above, it can be seen that when a cyclic sulfonic acid ester derivative compound is prepared by the preparation method according to the present disclosure, the yield is improved.

For reference, the peaks at 2.897 ppm and 2.738 ppm in NMR of Comparative Example are the peaks of residual DMF.

Figure 3A:
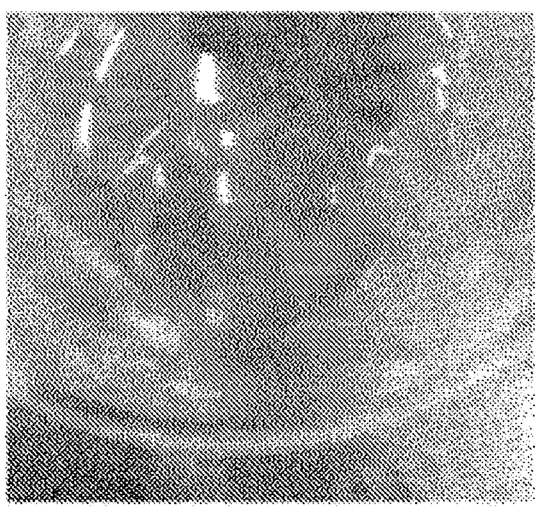
FIG. 3A is a digital camera photograph of a compound represented by Formula a and prepared in Example 1.
Figure 3B:
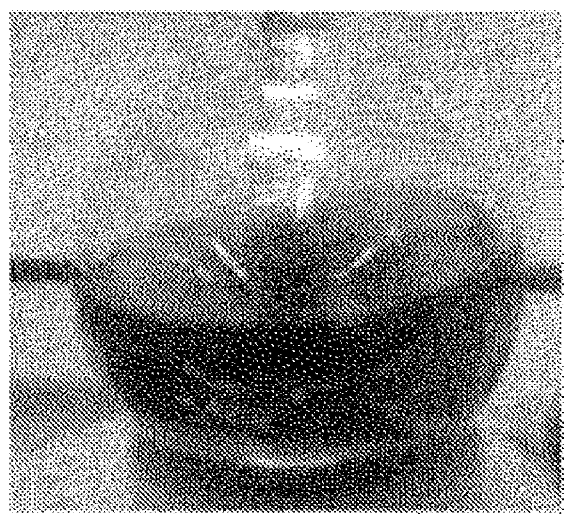
FIG. 3B is a digital camera photograph of a compound represented by Formula a and prepared in Comparative Example 1.

In addition, referring to FIGS. 3A and 3B which confirms the properties of a product (FIG. 3A is a digital camera photograph of the compound prepared in Example 1 and represented by Formula a, and FIG. 3B is a digital camera photograph of the compound prepared in Comparative Example 1 and represented by Formula a), it can be seen that when a cyclic sulfonic acid ester derivative compound is prepared by the preparation method according to the present disclosure, the properties (color purity) of the compound are improved.

The invention claimed is:

1. A method for preparing a cyclic sulfonic acid ester derivative compound, the method comprising:

step (A) reacting a compound represented by Formula 1 with thioacetic acid to prepare a compound represented by Formula 2; and step (B) subjecting the compound represented by Formula 2 to an oxidative cyclization reaction to prepare a compound represented by Formula 3:

[Formula 1]

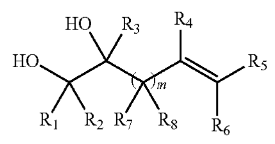

[Formula 2]

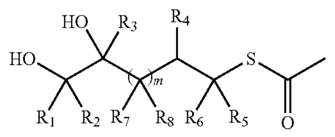

[Formula 3]

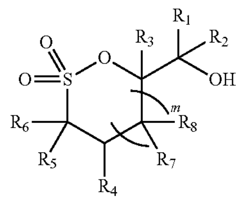

wherein in Formula 1 to Formula 3, m is 0 or 1, and $R_1$ to $R_8$ are each independently hydrogen, or a substituted or unsubstituted $C_1$-$C_{10}$ alkyl group.

2. The method of claim 1, wherein an equivalent ratio of the compound represented by Formula 1 to the thioacetic acid is 1:1 to 1:3.

3. The method of claim 1, wherein the step (A) is performed under an acid catalyst.

4. The method of claim 1, wherein the step (A) is performed in a polar aprotic solvent.

5. The method of claim 4, wherein the polar aprotic solvent is one or more of dichloromethane, chloroform, 1,2-dichloroethane, or acetonitrile.

6. The method of claim 1, wherein the step (A) is performed at a temperature of 20° C. to 40° C.

7. The method of claim 1, wherein the step (B) is performed under an acid catalyst.

8. The method of claim 1, wherein the step (B) is performed in a polar protic solvent.

9. The method of claim 8, wherein the polar protic solvent is one or more of distilled water, methanol, ethanol, propanol, or isopropanol.

10. The method of claim 1, wherein in the step (B), the oxidative cyclization reaction is performed under one or more oxidization agents selected from $H_2O_2$, HOCl, NCS, NBS, or $KHSO_5 \cdot 0.5KHSO_4 \cdot 0.5K_2SO_4$.

11. The method of claim 1, wherein the step (B) is performed at a temperature of 0° C. to 25° C.

12. The method of claim 1, wherein in Formula 1 to Formula 3, $R_1$ to $R_8$ are each hydrogen.

13. The method of claim 3, wherein the acid catalyst is trifluoroacetic acid (TFA), hydrochloric acid (HCl), or sulfuric acid ($H_2SO_4$).

14. The method of claim 1, wherein the step (A) is performed for 2 hours to 8 hours.

15. The method of claim 7, wherein the acid catalyst in the step (B) is added in an amount of 3 equivalents or more with respect to 1 equivalent of the compound represented by Formula 2.

16. The method of claim 11, wherein in the step (B), the temperature is maintained at 0° C. to 10° C. when introducing an oxidization agent.

17. The method of claim 1, wherein the step (B) is performed for 4 hours to 24 hours.

* * * * *